United States Patent [19]

Harui et al.

[11] Patent Number: 4,913,151
[45] Date of Patent: Apr. 3, 1990

[54] TOOL FOR PLACEMENT OF A MONITORING PROBE IN THE SCALP OF A FETUS

[76] Inventors: Norio Harui, 4902-46th Ave. South, Seattle, Wash. 98118; Howard M. Hochberg, 14474-156th Ave. NE., Woodinville, Wash. 98072

[21] Appl. No.: 293,941

[22] Filed: Jan. 5, 1989

[51] Int. Cl.⁴ ............................ A61B 5/00; A61B 5/02
[52] U.S. Cl. ..................... 128/634; 128/642
[58] Field of Search ............... 128/778, 698, 642, 633, 128/634, 785, 788

[56] References Cited
U.S. PATENT DOCUMENTS

| | | | |
|---|---|---|---|
| 3,910,271 | 10/1975 | Neward | 128/642 |
| 4,320,764 | 3/1982 | Hon | 128/642 |
| 4,644,957 | 2/1987 | Ricciardelli et al. | 128/642 |
| 4,658,825 | 4/1987 | Hochberg et al. | 128/642 |
| 4,686,996 | 8/1987 | Ulbrich | 128/642 |

Primary Examiner—Lee S. Cohen
Assistant Examiner—Scott Getzow

[57] ABSTRACT

The combination of a rigid, elongated applicator tool (200) and an elongated integral drive rod/probe (202). The drive rod/probe (202) is a rigid cable which includes a monitoring probe (204) with an extending spiral needle (206) at the front end thereof. At the rear end of the cable is a drive knob (236). The applicator tool (200) includes a hood element at the front end thereof which overlies the probe (204) and the needle (206) of the drive rod/probe (202) when the drive rod/probe (202) is positioned within the applicator tool (200). The applicator tool (200) includes a longitudinal slot (208) which permits insertion and removal of the drive rod/probe (202).

24 Claims, 3 Drawing Sheets

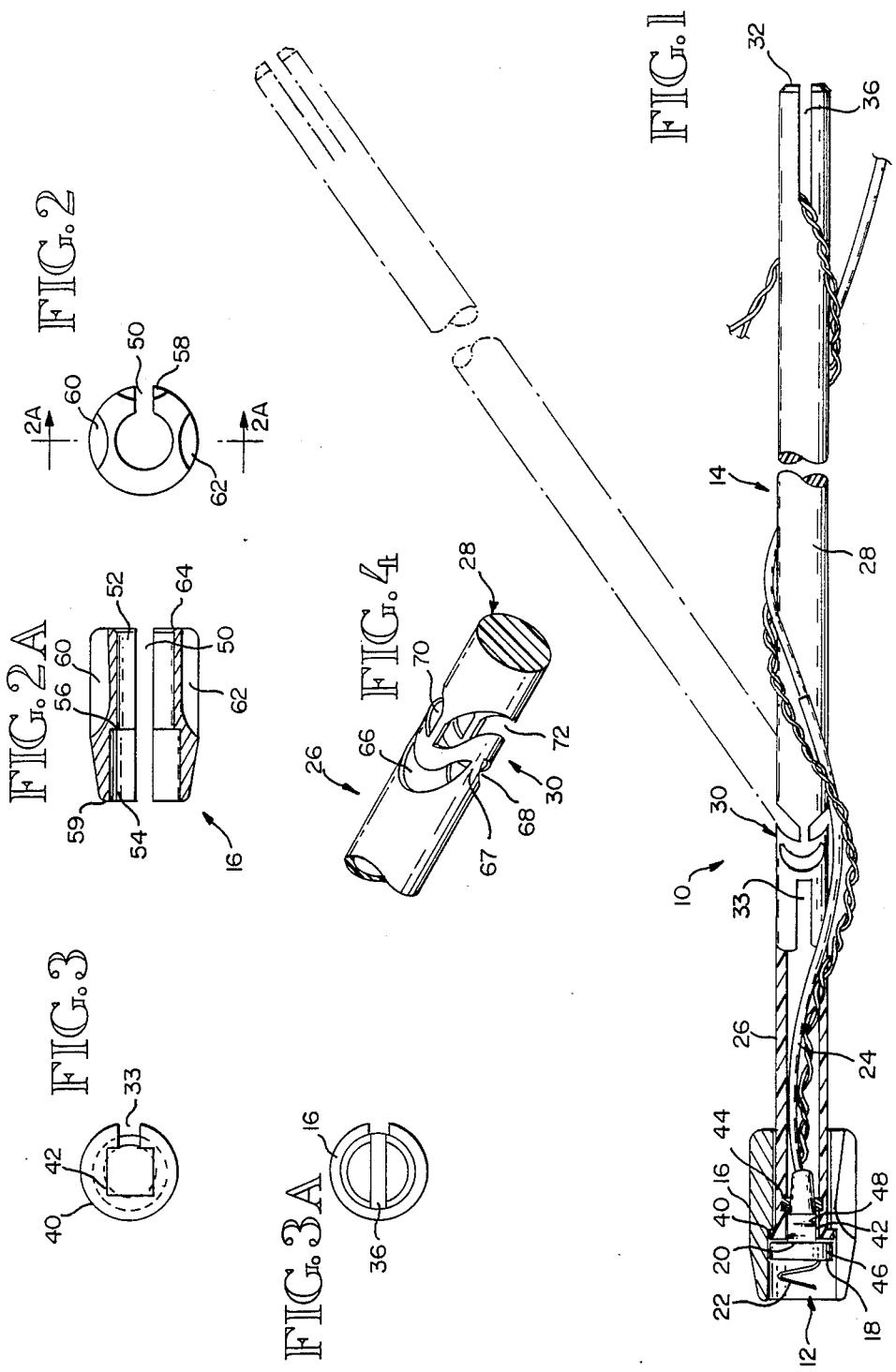

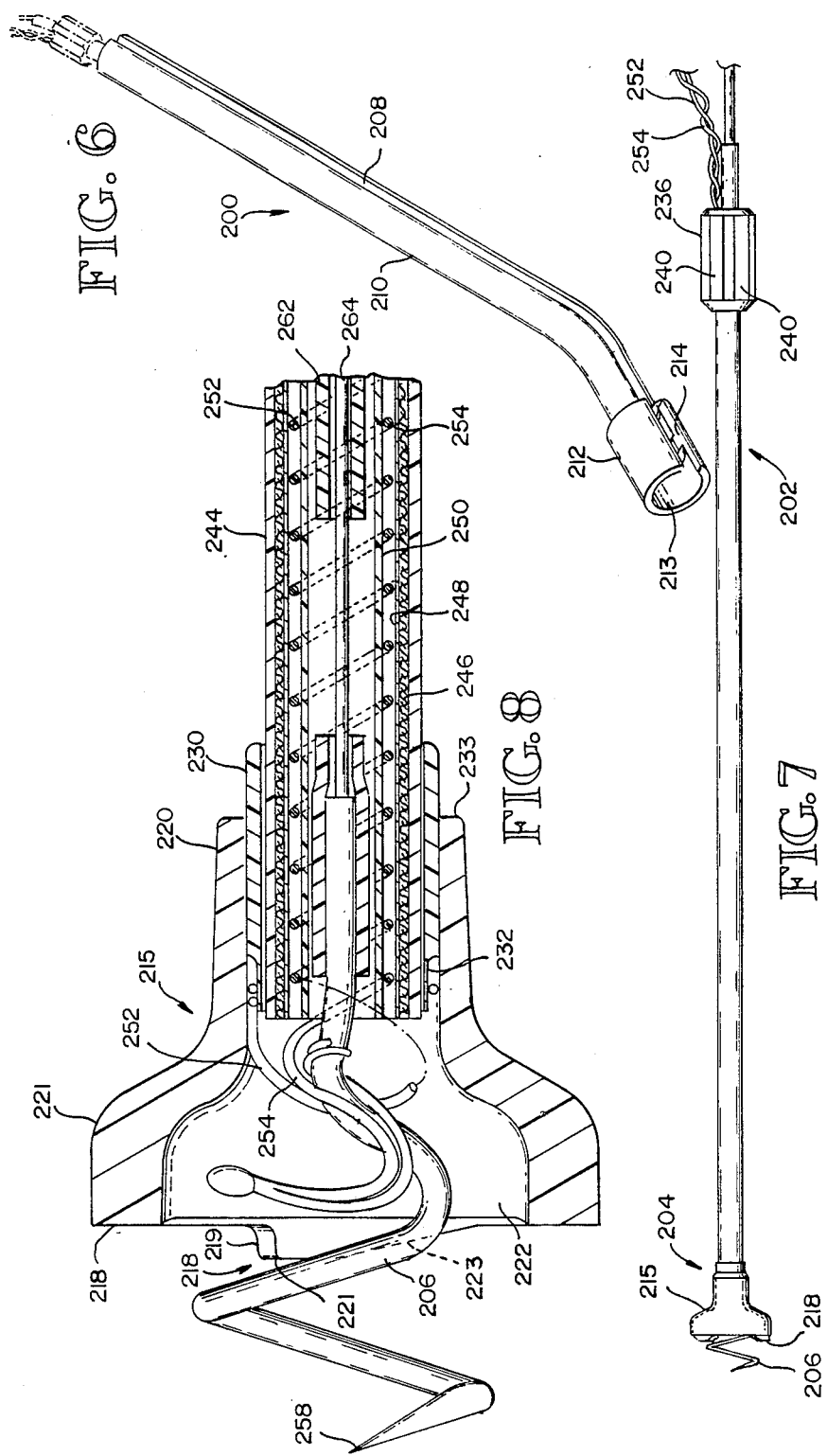

TOOL FOR PLACEMENT OF A MONITORING PROBE IN THE SCALP OF A FETUS

TECHNICAL FIELD

This invention relates generally to the art of fetal monitoring probes, and more particularly concerns an article for placement of such a probe in the scalp of a fetus.

BACKGROUND ART

The importance of monitoring the physical condition of a fetus during the birth process is well established. Appropriate remedial action and/or intervention can then be used when indicated. In this regard, the pH of the fetus, as well as the fetal heart rate, are important indicators of fetal condition. Fetal monitoring equipment has been developed to obtain, analyze and display such information. Typically, such information is obtained from the fetus by means of a probe which is attached to the scalp of the fetus in utero and which remains in the scalp tissue throughout the birth process. An example of such a probe is shown in U.S. Pat. No. 4,658,825 to Hochberg et al, which is assigned to the same assignee as the present invention.

In order to obtain reliable information, particularly for pH, it is necessary that the end portion of the probe containing the pH sensor be securely positioned in the scalp of the fetus. This is sometimes difficult, since the clinician must accomplish the initial attachment of the probe by feel rather than by sight, and the resulting attachment must be sufficiently strong to withstand the movement of the fetus and the mother during the birth process.

Although the particular shape (spiral) of the needle shown and described in the '825 patent has proved to be significant in maintaining the secure attachment of the probe to the fetal scalp, the guidance of the probe to, and initial positioning of the probe on, the fetal scalp is also important, as well as the ability to rotate the probe so that the spiral needle moves into the fetal scalp while maintaining the probe body at an angle which is substantially normal to the scalp. This is often difficult to do under actual conditions.

For that reason, an insertion/placement tool is typically used with the probe to attach the probe to the scalp. While existing insertion tools are typically flexible to accommodate the insertion of the probe through the vagina and cervix of the woman in labor to the fetal scalp, flexibility alone does not result in proper initial placement and subsequent maintenance of the attachment of the probe to the fetal scalp. In order to accomplish reliable attachment, the applicant has discovered that the forward end of the probe must be initially positioned substantially normal to the fetal scalp, and must be maintained in that position by the insertion tool, while at the same time the tool must be rotatable from its far end (opposite from the near or fetal scalp end), with the far end of the tool being at a substantial angle relative to the near end which is at the fetal scalp.

Use of existing tools have resulted in difficulty in properly attaching the probe to the fetal scalp, which in turn often results in inaccurate or unreliable readings, particularly of pH.

DISCLOSURE OF THE INVENTION

The article includes a drive element having a forward end which is adapted to support a probe element, wherein the probe includes a needle extending therefrom, wherein the drive element is flexible along its length, contains connections for the probe and includes means in the vicinity of the rear end thereof for rotating the drive element and hence the probe. The article further includes a rigid applicator tool which has a longitudinal slot along one side thereof, adapted to receive the drive element, including the probe, therein. The slot is large enough to accommodate the drive element.

BRIEF DESCRIPTION OF THE DRAWINGS

FIG. 1 is an elevational, partial cross-sectional view showing the article of one embodiment of the present invention.

FIG. 2 is a rear elevational view of the front hood element portion of the article of FIG. 1.

FIG. 2a is a cross-sectional view of the front hood element of FIGS. 1 and 2.

FIG. 3 is a front elevational view of the drive rod portion of the article of FIG. 1.

FIG. 3a is a rear view of the drive rod of FIGS. 1 and 3.

FIG. 4 shows the details of the flexure joint of the article of FIG. 1.

FIG. 6 is an isometric view of the applicator tool portion of another embodiment of the present invention.

FIG. 7 is a side elevational view of the integral drive rod/probe portion of the embodiment of FIG. 6.

FIG. 8 is an enlarged cross-section view of a portion of the drive rod/probe shown in FIG. 7.

BEST MODE FOR CARRYING OUT THE INVENTION

Figure 5:
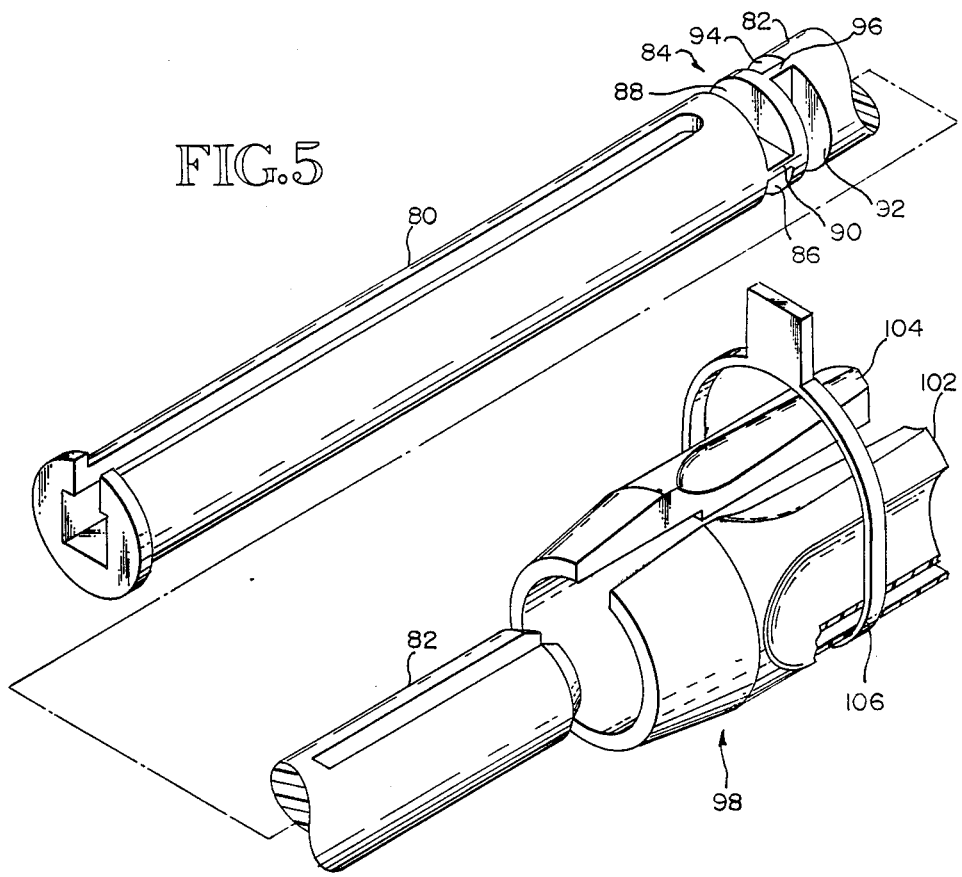
FIG. 5 is an isometric view of another embodiment of the insertion tool of the present invention, showing a different flexure joint configuration and a modified front hood element.

The insertion/placement tool of the present invention is shown generally at 10 in FIG. 1, in combination with a fetal probe shown generally at 12. The tool 10 generally comprises a drive rod 14 and a hood-like element 16 which is positioned at the front end 18 of the drive rod 14. The fetal probe 12 is shown operatively positioned in the drive rod, with the probe 12 in the embodiment shown generally comprising a body portion 20, an extending needle element 22 and electrical and optical connections 24. The electrical and optical connections 24, hereinafter referred to simply as cable connections, are in turn connected to a conventional fetal monitoring unit which analyzes and displays the information obtained by the probe.

In the embodiment shown, the drive rod 14 comprises a length of relatively stiff plastic, approximately 10 inches long and 0.37 inches in diameter. An example of suitable material is polypropylene. The drive rod 14 includes a first, forward section 26 which is relatively toward the fetus, and a second, rear section 28 which is relatively away from the fetus. The forward section 26 is hollow while rear section 28 is solid. The forward and rear sections are joined by a flexure joint 30 which is shown in more detail in FIG. 4 and described below.

The hollow forward section 26 in the embodiment of FIG. 1 is approximately 2½ inches long, and has a longitudinal slot 33 therein which communicates with the hollow interior of section 26 and which extends from the front end 18 of the drive rod approximately 2.40 inches toward the rear end thereof. The slot 33 is wide enough to permit the exit of the cables 24 of the probe from the interior of the drive rod 14. In the embodiment shown, slot 33 is straight; however, it could spiral around the circumference of the forward section of the drive rod, if desired. The solid rear section 28 also includes a longitudinal slot 36 which extends from the rear end 32 thereof approximately 0.80 inches. Slot 36 is designed to permit the cables 24 to be temporarily secured to the rear end of the drive rod when the probe is in position within the drive rod, and the rod is being inserted into the mother for placement of the probe on the scalp of the fetus.

At the front end 18 of the drive rod 14 is a hood retaining shoulder or lip 40 which is round in outline and approximately 0.45 inches in diameter, as shown in FIGS. 1 and 3 and also as shown in the embodiment of FIG. 5. The lip 40 extends outwardly from the exterior surface of the drive rod approximately 0.07 inches and is 0.06 inches thick. Lip 40 prevents the hood element 16 from coming off the front end of the drive rod.

The interior surface of the drive rod 14, from the front end 18 thereof for a distance of approximately 0.20 inches, is square in outline, approximately 0.20 inches on a side. At the rear end of this square portion 42 is a lateral groove 44 in the interior surface of the drive rod 14, approximately 0.10 inches wide and 0.28 inches in diameter. The remainder of the forward section 26 has an interior diameter of 0.22 inches. However, the interior surface of the drive rod could be square over the entire length of the forward section, if desired.

Referring to FIG. 1, the dimensions of the drive rod and the hood are adapted to the dimensions of the probe 12, so that for instance, front portion 46 of probe 12 has a diameter which is just slightly smaller than the interior diameter of the front portion of the hood 16, while middle portion 48 of the probe, which is square in cross-sectional outline, has cross-sectional dimensions which are slightly less than the dimensions of the square portion 42 of the interior surface of drive rod 14. The probe 12 thus fits securely in the drive rod at the front end thereof.

The front hood element 16 is shown in FIGS. 1, 2 and 2a. In the embodiment shown, the hood element 16 fits around the drive rod 14 at the front thereof, and extends beyond the front end 18 of drive rod 14 a sufficient distance to cover the extending needle portion 22 of the probe when the probe 12 is operatively positioned in the drive rod, as shown in FIG. 1. The hood element 16 in the embodiment shown is 1.2 inches long and is generally circular in exterior outline, with a diameter of approximately ¾ inches. A longitudinal slot 50 extends the entire length of the hood element and extends from the exterior surface of the element to the hollow interior thereof.

The slot 50 is wide enough to permit exiting of the cables 24 of the probe therethrough. The hollow interior of the front hood element 16 includes a rear cylindrical portion 52 which is approximately 0.70 inches long and has a diameter of 0.38 inches and a front cylindrical portion 54 which is approximately 0.50 inches long and has a diameter of 0.47 inches. The interior lip 56 defined at the junction of the front and rear portions 52 and 54 abuts against the rear surface of extending lip 40 on the front end 18 of the drive rod 14, which prevents further forward movement of the hood element 16 relative to the drive rod 14.

In use, the hood element 16 is grasped by the clinician and inserted into position into the body of the mother, against the head of the fetus, bringing the drive rod and the probe therealong. The fact that the front hood element 16 extends a slight distance beyond the forward tip of the probe needle 22 prevents the needle from damaging the mother's tissues during insertion of the probe. The front end 59 of the hood element may be serrated or otherwise configured to provide a friction surface. This results in the skin being held taunt to permit better needle penetration.

To facilitate the insertion of the tool and the probe by means of the hood element, the hood element 16 has three peripherally spaced cut-out portions 58, 60 and 62 in the outer surface thereof, which extend from the rear end 64 of the hood element 16 to a point which is slightly more than half way to the front end of the element. The three cutout portions 58, 60 and 62 are configured to accommodate the fingers of the clinician. Cutout portions 60 and 62 are spaced 180° relative to each other around the periphery of the hood element, while cutout 58 is at 90° to cutouts 60 and 62. Typically, but not necessarily, slot 50 divides cutout 58.

One embodiment of the flexure joint 30 which connects the first and second sections 26 and 28 of the drive rod 14 is shown in FIG. 4. The flexure joint 30 is defined by first and second grooves 66 and 68 and third and fourth grooves 70 and 72. First and second grooves 66 and 68 oppose each other, as shown in FIG. 4 and are somewhat crescent-shaped, extending around the circumference of the drive rod approximately 160°, toward the rear end thereof, leaving a short span of approximately 1/16 inch of material 67 between the respective interior ends of the first and second grooves 66 and 68. Grooves 66 and 68 at their widest are approximately ⅛ inch and narrow toward each end.

The third and fourth grooves 70, 72 are cut in the drive rod slightly to the rear of the first and second grooves 66 and 68. Grooves 70 and 72 also oppose each other and are at 90° relative to the first and second grooves. Grooves 70 and 72 are also crescent-shaped, extending toward the front end 18 of the drive rod, and are positioned relative to each other so that there is a small span of material between the respective interior ends of each groove.

The two sets of grooves are spaced so that there is approximately ⅛ inch of material between the respective sets of grooves. Also, the interior ends of the four grooves are in the same plane, at points 90° removed from each other. Accordingly, the resulting flexure joint acts somewhat like a universal joint, permitting the rear section 28 to be angled relative to the forward second 26 about relatively small, defined points, and further permitting rotation of the forward section 26 by rotating the rear section 28 without the drive rod being distorted in any way. This is illustrated in FIG. 1. The arrangement and configuration of the grooves is also such that rotation of the drive rod by the rear section 28 will result in a corresponding rotation of the forward section 26, without lateral movement of the forward section.

Other particular flexure joint configurations are possible. One other configuration is described in more detail below. It is important, however, that the flexure be able to permit angling of the rear section 28 relative to the forward section 26, without distortion of the first section, and such that rotation of the rear section 28 results in a corresponding rotation of the forward section 26. This has the advantageous result that when the rear section 28, which typically extends outwardly from the patient, is rotated by the clinician, the forward section of the probe, which is positioned against the scalp of the fetus, remains substantially normal to the fetal scalp during rotation of the drive rod, which in turn results in the secure attachment of the probe to the scalp of the fetus in a convenient and reliable way, as explained in more detail below.

FIG. 5 shows a somewhat different embodiment of the present invention. The drive rod shown in FIG. 5 includes a forward section 80 and a rear portion 82, with the forward section being hollow and the rear portion 82 being solid, as with the embodiment of FIGS. 1-4. The configuration of the forward and rear sections 80 and 82 is also substantially the same as for the embodiment of FIGS. 1-4. However, the flexure joint 84 is different. Joint 84 includes a first pair of grooves 86 and 88 which are approximately 3/16 inch wide, are in registry, and extend approximately halfway through the drive rod, at right angles to the longitudinal axis of the rod, leaving a thin center portion 90 approximately 1/32nd inch thick so that the rear section 82 can be moved relative to the forward section 80 about the thin center portion 90.

A second set of grooves 92 and 94 is located just to the rear of grooves 86 and 88. Grooves 92 and 94 are oriented at 90° to grooves 86 and 88, but otherwise have the same configuration. A thin center portion 96, which is at 90° relative to center portion 90, remains between the two grooves 92 and 94, permitting movement of the rear section 82 relative to the forward section 80 about center portion 96. The flexure joint 84 with the configuration shown permits a substantially universal joint function between the rear section 82 and the forward section 80.

The hood element 98 shown in FIG. 5 is also somewhat different than the hood element 16 of FIG. 1, in that it includes a lateral slot 100 which extends through the cross-sectional dimension of the element and also extends from the forward end 102 of the hood 98 to a point somewhat rearward of the rear end 103 of the finger depressions. In the embodiment shown, the slot 100 is located on the side of the element opposite to finger depression 104, which is designed to accommodate the middle finger of the clinician. A latex band 106 is positioned around the hood element as shown, a portion of the band 106 extending through slot 100. The dimension of the latex band 106 is such as to hold the middle finger of the clinician in depression 104. The middle finger of the clinician thus acts as a primary guide for the tool as it is inserted into the patient.

In use of the article of the present invention, in particular, the embodiment of FIG. 1, the probe must first be positioned in the drive rod. The probe cables 24 are first fitted through the longitudinal slot 50 in the hood element, and also through a portion of the slot 33 in the forward section 26 of the drive rod. The electrical (ECG) leads are directed through slot 32 at the rear of the drive rod, while the optical lead (pH) is not extended through the slot 32. The probe body itself is positioned in the open center of the hood element, and is then moved rearwardly so that the portion 48 of the probe is seated at the front end of the drive rod and portion 46 of the probe abuts the front surface of the lip 40 of the drive rod. As stated above, in such an arrangement, the hood element overlies the extended needle portion 22.

The insertion tool with the probe positioned therein is now ready for insertion and attachment of the probe onto the scalp of the fetus. To do this, the clinician grasps the hood element 16 in the cutout portions thereof, and guides the hood element and hence the drive rod and probe through the cervix and vagina of the woman in labor to the point where the end of the hood element contacts the scalp of the fetus. The hood element is placed against the scalp of the fetus at an angle which is normal thereto by judgment of the clinician. In the embodiment of FIG. 5, the latex band holds the index finger of the clinician in place on the cutout portion of the hood element and thus the index finger can be used as a "pointer" for insertion and proper placement of the probe.

While holding the hood element 16 in place, the clinician brings forward pressure at the rear end of the drive rod, while at the same time rotating the drive rod. This forces the probe and the extending needle forwardly and to rotate so that the needle is screwed into the scalp of the fetus. During this process, the hood element 16 and the flexure arrangement 30 prevents the probe from shifting on the scalp. A reliable attachment of the probe to the scalp thus occurs.

At the end of this process, the drive rod and hood element are simply pulled away from the probe, with the cables coming out by way of the slots. The insertion tool is then removed.

FIGS. 6 through 8 show a further embodiment of the present invention. This embodiment comprises the combination of an elongated applicator tool shown generally at 200 and an elongated integral drive rod/probe shown generally at 202. The drive/rod probe 202, which includes a monitoring probe 204 with an extending spiral needle 206 at the forward end thereof, is initially positioned within the applicator tool 200. A slot 208 extends for the length of the applicator tool 200, permitting insertion and removal of the drive rod/probe relative to applicator tool 200.

Referring to FIG. 6, which shows the applicator tool 200 in detail, the tool includes a guide tube portion 210, which in the embodiment shown has an exterior diameter of 0.375 inches. The longitudinal slot 208 is 0.15 inches wide. The guide tube portion 210 in the embodiment shown is made of a rigid, clear plastic tubing, such as PVC. It is angled or curved near one end thereof so as to better fit the average female anatomy, thereby facilitating installation of the probe in a direction perpendicular to the fetal scalp. At the forward end of applicator tool 200 is a hood element 212 which is also made of rigid, clear plastic. The hood 212 in the embodiment shown is approximately 0.8 inches long, and has an external diameter of 0.54 inches. The hood overlays the forward end of guide tube 210 by approximately 0.4 inches. The hood also includes a longitudinal slot 214 which has a width of 0.15 inches and which is arranged to be in registry with slot 208 of the guide tube 210. The internal diameter of the hood 212 at its forward end 213 is large enough to accommodate the monitoring probe 204 and needle 206 of the drive rod/probe 202. In the embodiment shown, the total length of the applicator tool is approximately 6.5 inches. As an alternative embodiment, it should be understood that a flexure joint could be incorporated in applicator tool 200 at a selected point along its length. The joint could be arranged to permit flexure in one axis of movement alone or in more than one axis.

The integral drive rod/probe is shown in FIGS. 7 and 8. The probe itself 204 includes an exterior casing or hub portion 215 having on its forward end surface 215 a plurality of spaced gripping feet 218. In the embodiment shown, the trailing edge 219 of each foot is relieved from side-to-side so that it extends laterally at an angle of approximately 5 degrees relative to a line normal to the circular peripheral edge of the forward end of the probe. The rear part 221 of the upper surface of each foot is flat, and is approximately 0.03 inches above the forward end surface 215 of the probe. Forward of the rear upper surface part 221 is a forward part 223 which slopes at an angle of approximately 15° (165° relative to the rear part 221) to the forward end surface 215 of the probe. In the embodiment shown, there are three gripping feet positioned at equally spaced intervals around the forward end surface, although a greater or perhaps fewer number could be used.

When the probe is rotated so that the sloped portion 223 of the gripping feet is the leading portion, rotation of the probe is relatively easy. When the probe has been rotated sufficiently that the needle is fully inserted into the fetal scalp and such that the rear part 221 of each gripping foot presses against the fetal scalp, it is quite difficult to rotate the probe in the opposite direction, because the blunt trailing edge (now the leading edge) tends to press into the scalp. The feet 218 improve the stability of the probe on the scalp of a fetus, particularly scalp with hair, and also reduce the possibility of the probe becoming loosened from the scalp after it has been initially attached. The hub 215 is generally circular in configuration, and in the embodiment shown has a length of 0.4 inches. The diameter of rear portion 220 of the hub is 0.23 inches, increasing to 0.46 inches for front portion 221. In the embodiment shown the hub 215 is made from a plastic material and is filled with epoxy 222.

At the rear of hub 215 is a reference electrode 230 which in the embodiment shown is a thin metal cylinder approximately 0.24 inches long and 0.180 inches in diameter. The reference electrode 230 has a front portion 232 which has a slightly smaller exterior diameter than the remainder thereof. The reference electrode 230 is positioned interiorly of the rear portion 220 of the probe hub 215, with the front portion 232 of the reference electrode extending almost to the point where the hub 215 begins to increase in diameter, approximately midway between the rear and front ends of the hub. This arrangement results in a small portion of the reference electrode 230 extending from the rear end 233 of the hub 215.

The drive rod portion 234 of the integral drive rod/probe extends axially through reference electrode 230, to a point just forward of the front edge thereof. The drive rod portion 234, which is in the form of a cable, as more clearly described hereinafter, is approximately 7 inches in length. At the rear of the cable is a drive knob 236 (FIG. 7). Drive knob 236 in the embodiment shown is generally cylindrical in configuration, approximately 0.31 inches in diameter and is approximately 0.6 inches long. Arranged around the exterior surface of the drive knob are a plurality of longitudinal grooves 240 which are generally configured to permit manipulation of the drive knob and hence the drive rod by human fingers. The interior of the drive knob is hollow, with the drive rod extending therethrough. The drive knob 236 is secured to the drive rod 202 so that the rod is rotated with the drive knob. The forward and rear edges of the drive knob are beveled, at 45° in the embodiment shown.

The arrangement of the drive rod is shown most clearly in FIG. 8. The drive rod, in the form of a flexible cable, includes an outer PVC jacket 244 and an outer braided sleeve conductor element 246 which provides torsional stiffness while maintaining low bend stiffness. The braided element 246, while an electrical conductor, is not electrically connected to any other element in the cable. The next layer is a thin anti-abrasion layer 248. Internally of layer 248 is a first internal sleeve 250, which is Teflon in the embodiment shown, around which is wound two alternating wires 252 and 254. The wires 252 and 254 provide the electrical connections for the probe, and extend out the rear of the integral drive rod/probe as shown in FIG. 7.

In the embodiment shown, wires 252 and 254, which provide the ECG connection, wind alternately around the Teflon sleeve 250 and then extend outwardly from the front end of the cable within the volume defined by the hub 215. One wire 254 is connected through a solder connection to the spiral needle 206, which extends out from the forward end of the hub 215 and which is held in place within the hub by conventional potting 222. In one embodiment, the spiral needle is approximately 1 complete turn, and extends approximately 0.16 inches beyond the forward end of the hub 215. The other wire 252 is electrically connected, such as by soldering, to the reference electrode 230. Extending down the middle of the cable is a second internal Teflon sleeve 262. Within Teflon sleeve 262 is a fiber optic cable 264 which extends through the center of the spiral needle 206 and connects with a pH detector element located near the pointed end 258 of the spiral.

In use, the integral drive rod/probe 202 is positioned within the applicator tool 200, the diameter of the drive rod, i.e. cable, being of such a size as to fit into the applicator tool through the slot 208. The hood element 212 at the forward end of the applicator tool covers the front end of the hub 215 and the extending needle 206, protecting the patient from possible injury during insertion of the probe. As mentioned above, the applicator tool is rigid and sufficiently long to allow good control of the tool, and is curved to better fit the female anatomy. When the front end of the hood 212 is positioned squarely on the scalp of the fetus, the drive knob 236 is moved forwardly and then rotated so that the needle turns into the fetal scalp. The slot 208 in the guide tube portion of the applicator tool is on one side thereof so as to contain the drive cable in both directions in the plane of the bend. The friction of the cable against the bent portion of the guide tube will tend to roll the cable to the side as it is rotated. The slot 208 is located in the side opposite from the direction of the roll.

When the needle has been fully inserted so that the front end of the hub 215 is adjacent the fetal scalp, the applicator tool is removed by moving the drive knob 236 toward the side of the applicator tool and then withdrawing the tool from the drive cable through the longitudinal slot in the tool. The cable may thereafter be used to tighten the probe should it become loose, by rotating the probe in one direction, or to remove the probe, when necessary or desirable, by rotating it in the opposite direction.

Thus, an article has been described which results in a convenient, reliable and correct (i.e. the probe is positioned normal to the scalp) attachment of a probe to the scalp of a fetus.

Although a preferred embodiment of the invention has been disclosed herein for illustration, it should be understood that various changes, modifications and substitutions may be incorporated in such embodiment without departing from the spirit of the invention as defined by the claims which follow.

We claim:

1. An article for securely attaching a monitoring device to the scalp of a fetus, comprising:
   a probe including a spiral needle element and connections extending therefrom;
   a drive element having a forward end supporting the probe and a rear end, the drive element being flexible along its length and containing therewithin said connections for the probe, the drive element including means in the vicinity of the rear end thereof for rotating the drive element and hence the probe;
   a rigid applicator tool receiving the drive element and the probe, the applicator tool having a longitudinal slot along one side thereof of sufficient width to accommodate passage of the drive element therewithin.

2. The article of claim 1, wherein the applicator tool is angled.

3. The article of claim 1, wherein the drive element is a cable.

4. The article of claim 3, wherein the connections include at least a first and a second electrical connection for monitoring of ECG, and a fiberoptic connection for monitoring of pH.

5. The article of claim 4, wherein the probe includes a hub portion from which the spiral needle extends and a reference electrode portion at a rear of the hub portion, wherein the drive element fits securely within the reference electrode and wherein the first electrical connection includes an electrical conductor connected to the reference electrode and the second electrical connection includes an electrical conductor connected to the spiral needle element.

6. The article of claim 5, wherein the drive element is a cable which includes an interior sleeve, wherein the two electrical connections are wound around the interior sleeve, and wherein the fiberoptic connection extends interiorly of said sleeve.

7. The article of claim 6, wherein the cable includes a cable braid which provides torsional stiffness while maintaining low bend stiffness.

8. The article of claim 1, wherein the applicator tool includes a front end corresponding to the forward end of the drive element, and includes a hood element in the vicinity of the front end thereof, which overlays the probe and the spiral needle when the drive element is in position within the applicator tool and which assists in the positioning of the probe normal to the fetal scalp.

9. The article of claim 1, wherein said applicator tool includes a flexure joint at a selected location along its length.

10. The article of claim 1, including a plurality of gripping feet on a forward end of the probe, wherein the gripping feet have a blunt end and a sloping opposing end, so that rotation of the probe in the direction of the blunt end is difficult when the probe is inserted into the scalp of the fetus.

11. An article for securely attaching a probe to the scalp of a fetus, comprising:
    a probe including means for attaching the probe to the scalp of a fetus;
    an elongated drive element having a front end thereof, supporting the probe while the probe is being attached to the scalp of the fetus, wherein the drive element includes a joint along its length which separates the drive element into front and rear portions, wherein the front portion is hollow for receiving the probe therein and the rear portion is solid, wherein the joint is configured to permit the rear portion of the drive element to be angled relative to the front portion thereof without distortion of the front portion and without imparting a bending force to the front portion and further such that rotation of the rear portion results in corresponding rotation of the front portion without lateral movement of the front portion, including the probe, even when the rear portion is angled relative to the forward portion.

12. The article of claim 11, wherein the front portion of the drive element includes a front end, including a hood element around the front end of the front portion of the drive element for guiding the drive element and the probe to the scalp of the fetus, wherein the drive element and the hood element are configured and arranged to permit disengagement of the probe from the drive element.

13. The article of claim 12, wherein said joint includes two sets of opposing grooves positioned relatively close to each other and at 90° relative to each other around the circumference of the drive element.

14. The article of claim 12, wherein said joint includes a plurality of grooves, arranged and configured such that the rear portion of the drive element may be moved relative to the joint in such a manner as to define a cone.

15. The article of claim 12, wherein the rear portion of the drive element includes a longitudinal slot therein opening onto the rear portion of the drive element, to accommodate a probe cable.

16. The article of claim 12, wherein the hood element and a portion of the drive element in the vicinity of the front end thereof each include a longitudinal slot for removal of the probe from the drive element.

17. The article of claim 13, wherein the hood element includes portions in the outer surface thereof configured so as to accommodate the fingers of a clinician user.

18. The article of claim 15, including means for holding at least one finger of the user in one of said portions in the outer surface of the hood element.

19. The article of claim 18, wherein said holding means includes an elastic band, said elastic band extending through an opening in the hood element, tending to maintain the band with the hood element.

20. The article of claim 17, wherein the front end of the hood element is configured to provide a frictional contact between the hood element and the fetal scalp, thus tending to maintain the scalp taunt underneath the hood element.

21. The article of claim 17, wherein the probe includes a needle portion extending therefrom and the hood element extends beyond the front end of the drive element to overlie the needle portion and thereby prevent contact between the needle portion and the tissues of the mother while the probe is being inserted.

22. The article of claim 21, wherein the interior surface of the drive element in the vicinity of the front end thereof is configured to mate with the exterior configuration of a portion of the probe.

23. A probe for monitoring a fetus, comprising:

a probe body having a forward end surface;

a spiral-shaped needle element which extends from the forward end surface of said probe body and away from said probe body; and a plurality of generally saw-toothed shaped gripping feet members arranged at spaced intervals on the forward end surface of the probe body, the gripping feet each having a sloping leading end and an opposing blunt trailing end, so as to substantially prevent the probe body from being turned in a direction opposite from that for insertion of the probe body, following insertion of the probe body into the scalp of the fetus.

24. The article of claim 23, wherein the gripping feet are approximately 0.03 inches high and the sloping leading end has an angle of approximately 15°.

* * * * *